United States Patent
Neeb et al.

(10) Patent No.: US 11,478,388 B2
(45) Date of Patent: Oct. 25, 2022

(54) ADULT INCONTINENT DEVICE

(71) Applicant: APLIX, INC., Charlotte, NC (US)

(72) Inventors: Alexander James Neeb, Charlotte, NC (US); Michael Dan Brower, Charlotte, NC (US); Donald Harley Lester, Charlotte, NC (US); Andrew Robert Horne, Fort Mill, SC (US)

(73) Assignee: APLIX, LeCellier (FR)

( * ) Notice: Subject to any disclaimer, the term of this patent is extended or adjusted under 35 U.S.C. 154(b) by 1093 days.

(21) Appl. No.: 16/115,933

(22) Filed: Aug. 29, 2018

(65) Prior Publication Data

US 2019/0070048 A1   Mar. 7, 2019

Related U.S. Application Data

(60) Provisional application No. 62/553,299, filed on Sep. 1, 2017.

(51) Int. Cl.
| | |
|---|---|
| *A61F 13/15* | (2006.01) |
| *A61F 13/56* | (2006.01) |
| *B32B 5/02* | (2006.01) |
| *B32B 5/26* | (2006.01) |
| *A61F 13/49* | (2006.01) |
| *A61F 13/474* | (2006.01) |

(52) U.S. Cl.
CPC .... *A61F 13/5616* (2013.01); *A61F 13/15756* (2013.01); *A61F 13/474* (2013.01); *A61F 13/4902* (2013.01); *A61F 13/49015* (2013.01); *B32B 5/022* (2013.01); *B32B 5/26* (2013.01)

(58) Field of Classification Search
CPC ........... A61F 13/5616; A61F 13/15756; A61F 13/474; A61F 13/49015; A61F 13/4902; B32B 5/022; B32B 5/26
See application file for complete search history.

(56) References Cited

U.S. PATENT DOCUMENTS

| | | |
|---|---|---|
| 6,255,236 B1 | 7/2001 | Cree et al. |
| 2010/0096074 A1 | 4/2010 | Schoenbeck et al. |
| 2015/0257945 A1* | 9/2015 | Pagnoni ................ A61F 13/622 604/385.16 |

FOREIGN PATENT DOCUMENTS

| | | | | |
|---|---|---|---|---|
| EP | 2689760 A1 | 1/2014 | | |
| WO | WO-2010098793 A1 * | 9/2010 | ............ | B32B 27/32 |
| WO | WO 2014/179370 A1 | 11/2014 | | |

\* cited by examiner

*Primary Examiner* — Jacqueline F Stephens
(74) *Attorney, Agent, or Firm* — Hammer & Associates, P.C.

(57) ABSTRACT

A wing for an adult incontinent device is disclosed. The adult incontinent device has a chassis with a lateral attachment surface. The wing includes a stretch laminate with at least one nonwoven layer and at least one elastic layer. The nonwoven layer and the elastic layer are bound together in face-to-face contact. The stretch laminate has at least one stretch zone and at least one non-stretch zone. The stretch laminate has no overlap portions between the stretch zone and the non-stretch zone. One end of the wing is affixed to the lateral attachment surface of the chassis.

33 Claims, 7 Drawing Sheets

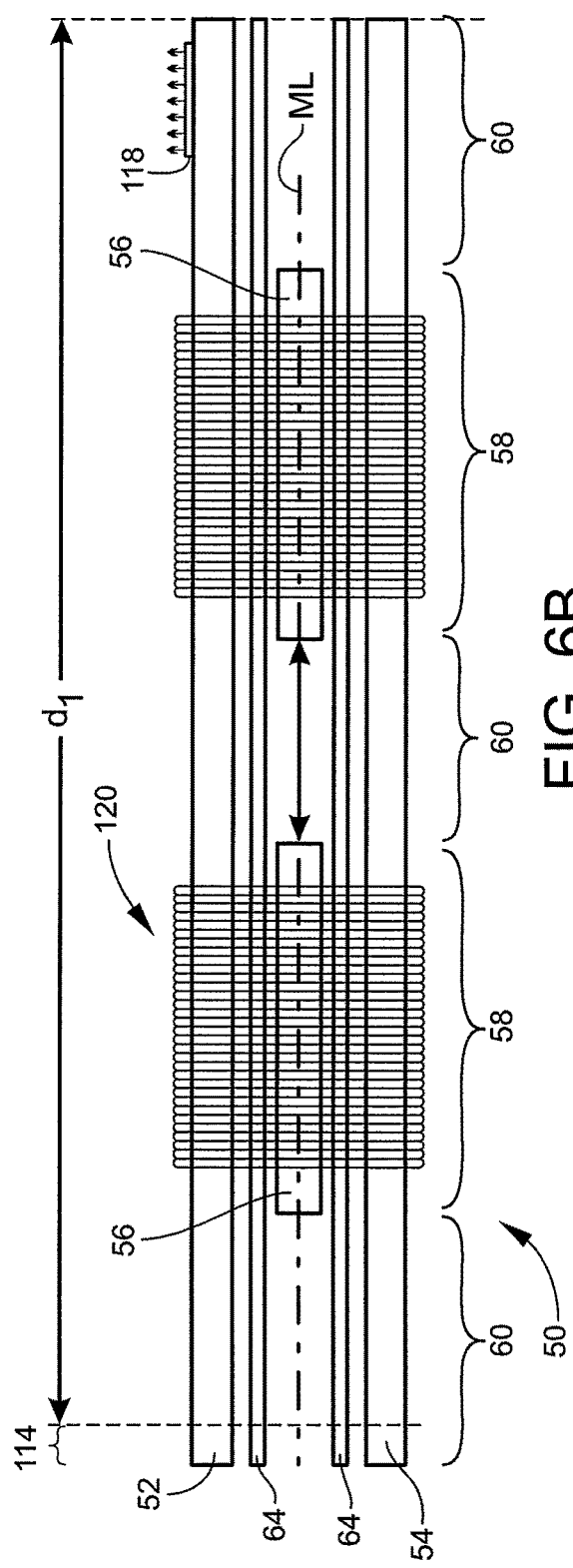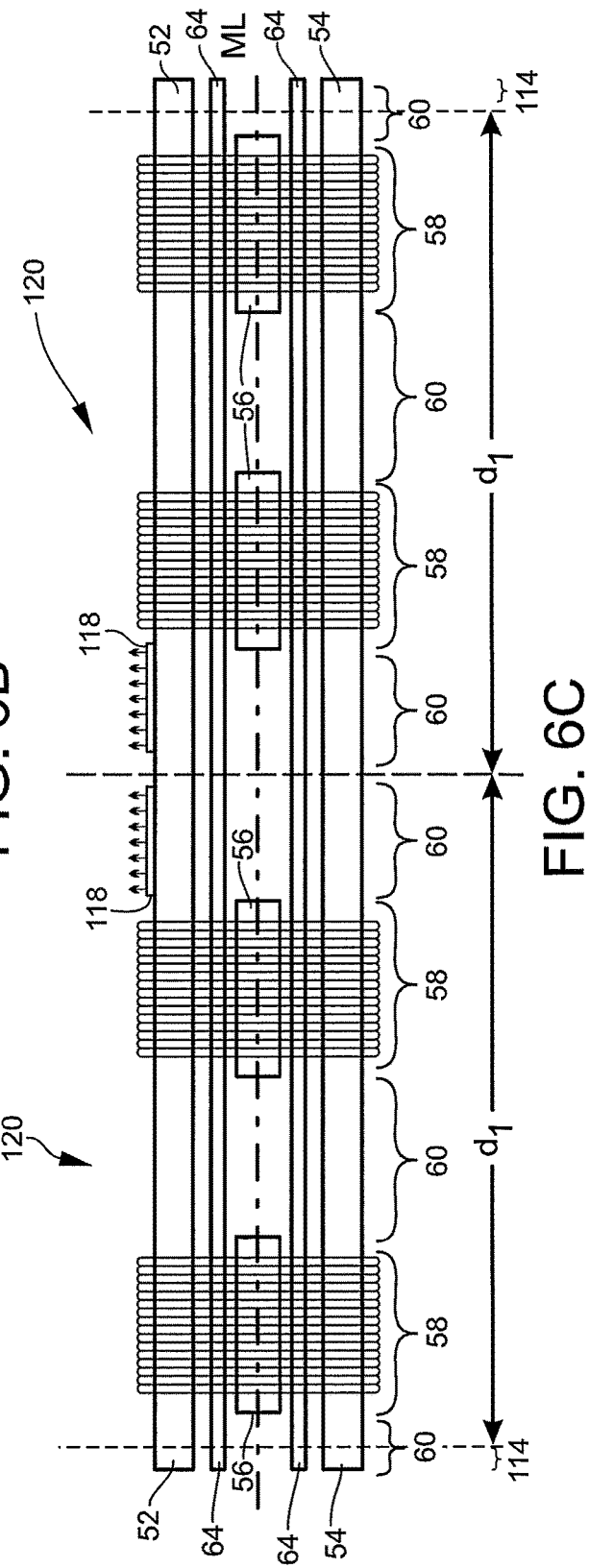

ADULT INCONTINENT DEVICE

RELATED APPLICATION

This application claims the benefit of U.S. Provisional Patent Application Ser. No. 62/553,299 filed Sep. 1, 2017, incorporated herein by reference.

FIELD OF THE INVENTION

The invention is generally directed to adult incontinent devices, particularly the 'wings' used in those devices.

BACKGROUND OF THE INVENTION

The incontinent device market may be divided into two segments, baby devices (or diapers) and adult devices (or briefs). The baby and adult segments are different because of many factors including, but not limited to: wearer considerations (babies versus adults), purchasers (parents versus wearer), and needs (toilet training for babies versus medical needs for adults). Accordingly, the innovation drivers for these two segments are different and cannot be conflated.

In the adult incontinent device market, the current products need improvement. For example, the components used to fasten the device around the adult wearer, typically a wing, are wanting from a manufacturing point of view and a utility point of view. Currently, the wings used on adult incontinent devices are made from two or more subcomponents that must be joined together before attachment to the device. Such multi-component wings, at least, increase the complexity (and cost) of manufacture, and render a less attractive device.

In FIGS. 1A and 1B, such a prior art device is illustrated. In FIG. 1A, device 10 has a chassis 12 including an attachment surface 14, and a wing 20 attached, via a bond 16, to the chassis 12. The wing 20 is made from several subcomponents, e.g., first non-stretch zone 22 overlapping and joined to stretch zone 26 overlapping and joined to second non-stretch zone 24. The device 10 may include a fastener (or fastener component) 18 at the distal end of wing 20. In FIG. 1B, the overlapping components are illustrated in cross-section based on a partial cross-section of the FIG. 1A. At the overlaps (or seams) 28, 30, the subcomponents are joined together. These overlaps (or seams), at least, increase the complexity of manufacture, increase waste by underutilizing a portion of the subcomponent, decrease the attractiveness of the device, decrease the comfort of the device, and increase the risk of skin irritations by friction. In addition, the device with such overlaps introduces winding and unwinding difficulties due to different thickness of the product packaged on a roll. Additionally, such multi-components wings introduce insecurity for the user. For example, the joint between the two adjacent components may unintentionally break during the use of the device, thereby putting the user in a difficult/uncomfortable/embarrassing position.

Accordingly, there is a need for new wings for use in adult incontinent devices (or briefs).

DESCRIPTION OF THE DRAWINGS

For the purpose of illustrating the invention, there is shown in the drawings a form that is presently preferred; it being understood, however, that this invention is not limited to the precise arrangements and instrumentalities shown.

FIGS. 6A, 6B, and 6C illustrate embodiments of the invention.

SUMMARY OF THE INVENTION

A wing for an adult incontinent device is disclosed. The adult incontinent device has a chassis with a lateral attachment surface. The wing includes a stretch laminate with at least one nonwoven layer and at least one elastic layer. The nonwoven layer and the elastic layer are bound together in face-to-face contact. The stretch laminate has at least one stretch zone and at least one non-stretch zone. The stretch laminate has no overlap portions between the stretch zone and the non-stretch zone. One end of the wing is affixed to the lateral attachment surface of the chassis.

DESCRIPTION OF THE INVENTION

Referring to FIGS. 2A, 2B, 3A, 3B, 3C, 6A, 6B, and 6C, several exemplary embodiments of the instant invention are illustrated. Like numerals are used for like elements.

Figure 2A:
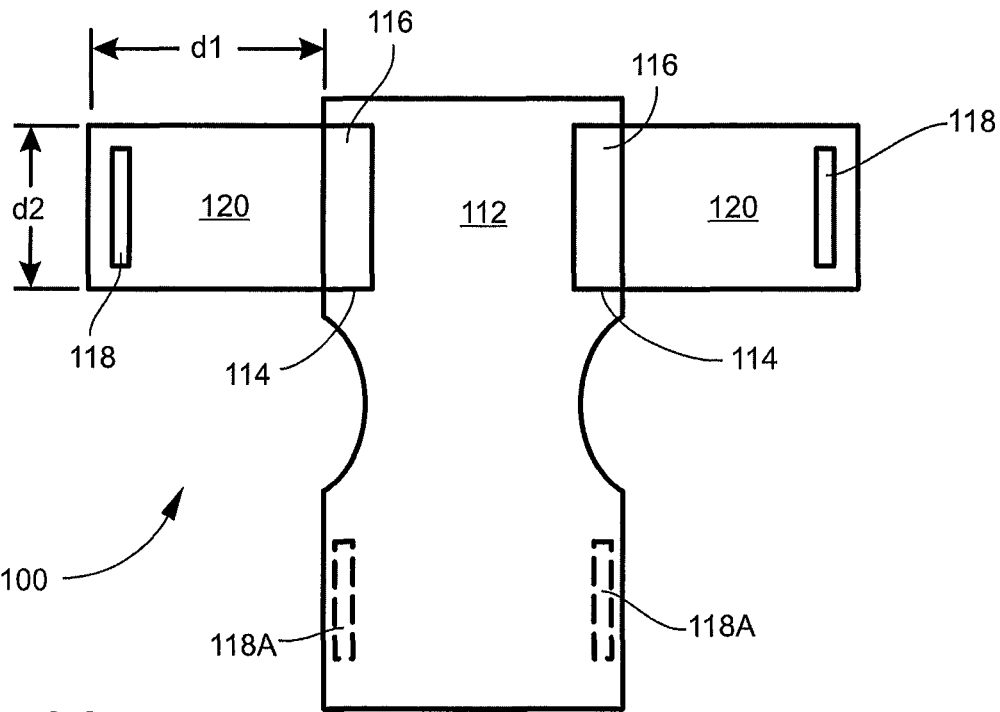
FIGS. 2A and 2B illustrate embodiments of adult incontinent devices utilizing embodiments of the instant invention.
Figure 2B:
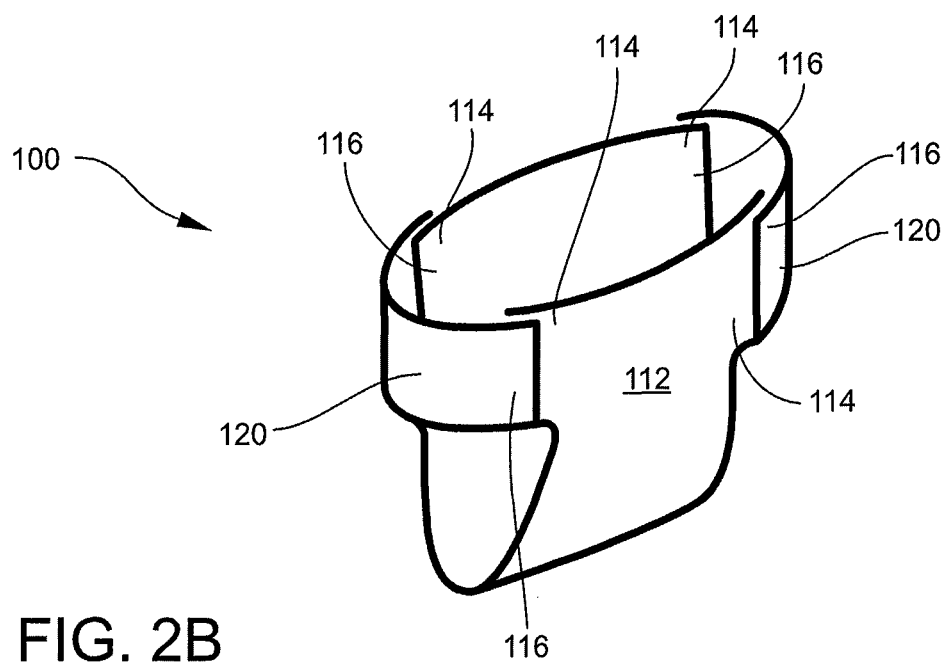

Referring to FIGS. 2A and 2B, two embodiments of the adult incontinent device 100 are illustrated. The device 100 generally includes a chassis 112 (conventional) with wings 120 affixed thereto, in particular two wings. In FIG. 2A, the device is closable, meaning that on the free (or distal) end of wing 120 is added a fastener component (e.g., hook & loop fastener and/or adhesive) 118 (and a mate 118A, if necessary, on another part of the chassis) that allows multiple openings and closing of the device, and the fixed (or proximal) end is affixed (in any conventional manner—e.g., bonded 116 with adhesive, thermal weld, ultrasound weld, stitching) to the attachment surface 114 of the chassis 112. In FIG. 2B, the device 100 is closed, meaning that both ends of the wing 120 are fixedly attached (in any conventional manner—e.g., bonded 116 with adhesive, thermal weld, ultrasound weld, stitching) to the attachment surfaces 114 of the chassis 112. Thereinafter for convenience, the invention will be discussed with reference to the embodiment shown in FIG. 2A, but the invention is equally applicable to either embodiment.

Figure 3A:
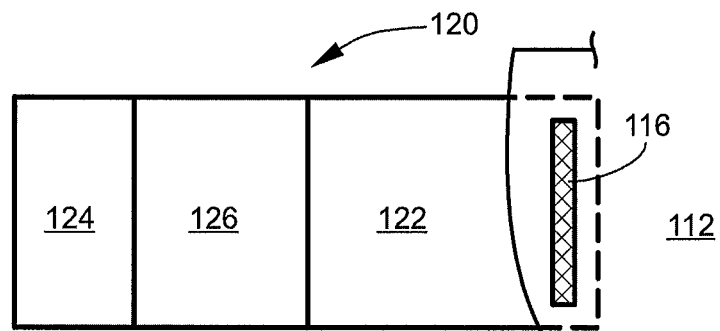
FIGS. 3A, 3B, and 3C illustrate various embodiments of the instant invention.
Figure 3B:
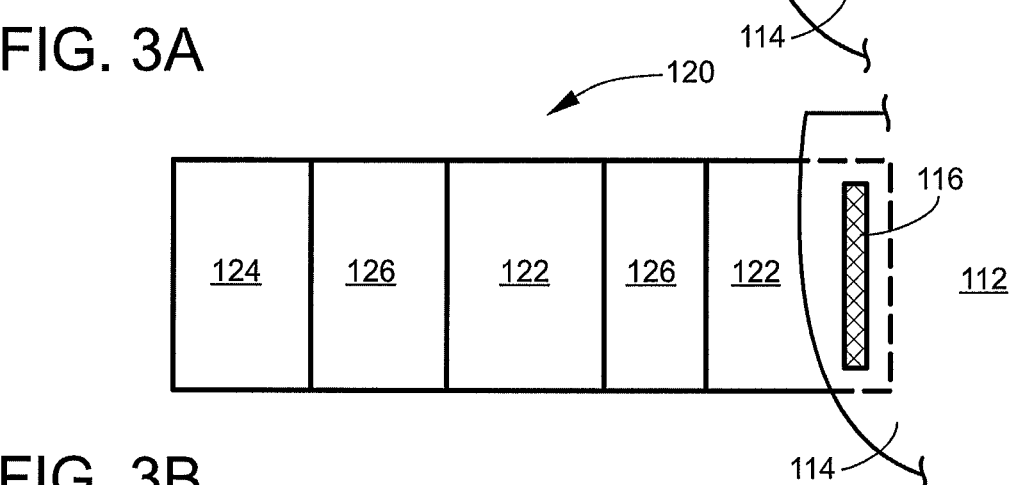
Figure 3C:
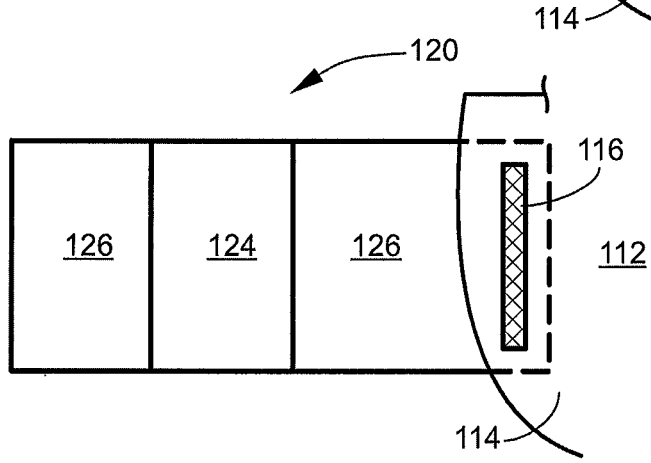

Referring to FIGS. 3A, 3B, and 3C, several embodiments of wing 120 are illustrated. Wing 120 generally includes at least one stretch zone 126 and one non-stretch zone 122 and/or 124. The stretch zone 126 and non-stretch zones 122, 124 may alternate with one another. The wing 120 has no overlaps (or seams), as discussed above, and may be made using a continuous layer (from one lateral side to an opposite lateral side) of nonwoven, i.e., no overlap or seam. The wing 120 is an integral (or unitary or seamless) component with no seams joining the subcomponent, i.e., the stretch zone 126 and the non-stretch zones 122, 124. Wing 120 may be a stretch laminate or a stretch laminate with at least one stretch zone and at least one non-stretch zone. A stretch zone may be elastic in at least the cross-machine direction (CD). The non-stretch zone may be non-elastic (or non-stretchable) in at least the cross-machine direction. Each wing has at least one elastic layer. The wing may have two, or at least two, elastic layers. The wing may have three, or at least three, elastic layers. The wing may have four, or at least four, elastic layers. A stretch laminate may comprise four elastic layers from which two wings may be formed. When a prior art wing is compared to the inventive wing, for the same extension, the width of the inventive wing may be less than the width of the prior art wing.

The stretch laminate may be any stretch laminate. Stretch laminate generally refers to a material comprising a nonwoven layer and an elastic layer bonded together in face-to-face contact. The bonding may be autogenous and/or facilitated by adhesives and/or welding (e.g., thermal, ultrasonic, or both). In the stretch laminate, the area of the elastic layer (or film) may be less than the area of the nonwoven layer, whereby elastic lanes (or zones) are created between inelastic lanes (or zones). The elastic lanes may be activated, non-activated, partially activated (activated over only a portion of the elastic lane) and/or activated to varying degrees. Activation may be accomplished by stretching (e.g., ring rolling). In some embodiments, the stretch laminate includes a top nonwoven, a bottom nonwoven with an elastic film sandwiched therebetween. Thereinafter for convenience, the stretch laminate 120 will be described as the latter.

Figure 4:
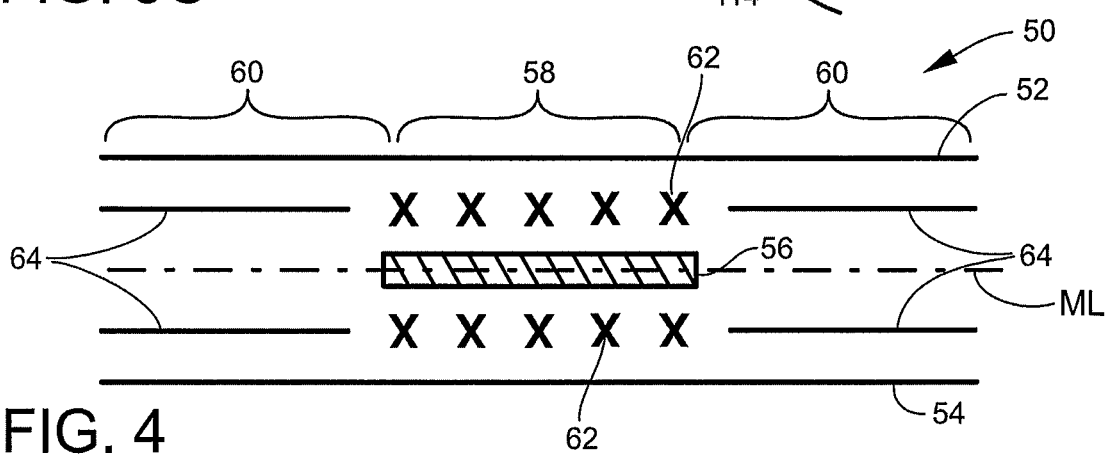
FIG. 4 illustrates an embodiment of a stretch laminate used in the instant invention.

One embodiment of a portion of a stretch laminate 50 is illustrated in FIG. 4. Stretch laminate 50, shown exploded, generally includes a top nonwoven 52, a bottom nonwoven 54, and an elastic film 56 sandwiched therebetween. The portion 58 of the stretch laminate with the elastic film defines the stretch zone (or elastic lane), and the portion 60 of the stretch laminate without the elastic film defines the non-stretch zone (or inelastic lane). In the stretch zone 58, the nonwovens 52, 54 are bonded to the elastic film via a bond pattern 62, so that the elasticity of the film is not impeded (or only partially impeded) by the nonwovens. In the non-stretch zone, 60, the nonwovens 52, 54 are bonded together via a bond pattern 64 and/or by use of a stiffening material (e.g., non-elastic film or foil), so that any possible stretchability of the bonded nonwovens is reduced or eliminated. The non-stretch zone may comprise two nonwoven layers that is fixed between them by fixing means selected from the group consisting of an adhesive layer, an ultrasonic bonding, thermo-calendering, cold calendering or a combination thereof. The non-stretch zone may comprise an additional material as reinforcing material between the two nonwoven layers. The non-stretch zone may not have to require an additional material for integrity or reinforcement as the two fixed nonwoven layers will be of adequate strength, corresponding to the non-stretch zone. Regarding stretch laminates, in general, reference is made to U.S. Pat. No. 7,794,819, which is incorporated herein by reference. The bond pattern 64 may be any bond pattern. The bond pattern 64 may be made with adhesives and/or welding (heat and/or ultrasonic).

The stretch zone, the elastic layer, and the non-stretch zone each have a width. In the stretch zone, the width of the elastic layer may be equal to the width of the non-stretch zone, and/or the width of the elastic layer maybe within the range of 25-90% of the non-stretch zone, and/or the width of the elastic layer may be within the range of 40-80% of the width of the non-stretch zone. For example, if the inventive wing is 300 mm wide and has 2 elastic films, each with a 45 mm width, then the elastic film is 43% (90/(300−90)×100=43% [stretch:non-stretch ratio]; if the inventive wing is 225 mm wide and has 2 elastic films, each with a 45 mm width, then the elastic film is 67% (90/(225−90)×100=67% [stretch:non-stretch ratio]; if the inventive wing is 215 mm wide and has 2 elastic films, each with a 45 mm width, then the elastic film is 72% (90/(215−90)×100=72% [stretch:non-stretch ratio]; if the inventive wing is 205 mm wide and has 2 elastic films, each with a 45 mm width, then the elastic film is 78% (90/(205−90)×100=78% [stretch:non-stretch ratio]

Nonwoven refers to any nonwoven. The nonwoven may be: a carded nonwoven, an air laid nonwoven, a wet laid nonwoven, a melt-blown (M) nonwoven, a spunbonded (S) nonwoven, a spunlaced nonwoven, a combined M and S nonwoven (for example, SM, SMS, SMMS, SSMMS), and/or combinations thereof. In one embodiment, the nonwoven is a spunbond nonwoven. The fibers (staple and/or filament) may be made of any material, for example, polyester (e.g., PET), polyamide (e.g., nylon), polyolefin (e.g., PE, PP), copolymers thereof, or a blend thereof. In one embodiment, the nonwoven may have a basis weight in the range of 10-40 g/m$^2$, and in another embodiment, in the range of 22-30 g/m$^2$. The top and bottom nonwovens may be the same or different. The nonwoven may have apertures or be in a precut form.

Elastic refers to any elastic material. The elastic films may be made from any elastomeric polymer mainly a thermoplastic elastomer. In one embodiment, the elastomeric polymers may be styrenic block copolymers. Styrenic block copolymers include, but are not limited to, SIS (styrene-isoprene-styrene) block copolymers, SBS (styrene-butene-styrene) block copolymers, or SEBS (Styrene-Ethylene-Butene-Styrene) or oleophilic elastomer based as for example Vistamaxx™ polymer available by ExxonMobil Chemical and combinations thereof. The elastic film may have any basis weight, in one embodiment, of 20-100 g/m$^2$, and in another 40-100 g/m$^2$, or in another 30-90 g/m$^2$ or in another 40-70 g/m$^2$. The elastic film could be a unique elastic film structure or a multilayer elastic film structure comprising an elastic film structure and at least one layer of skin layer structure or at least an elastic film structure in sandwich between two skin layer structures.

In FIG. 3A, a first embodiment of the wing 120 is shown. Wing 120 has one stretch zone 126 between two non-stretch zones, 122, 124. The one (or proximal) end, e.g., a non-stretch zone, of the wing 120 is affixed to the attachment surface 114 of the chassis 112 via bond 116. The other (or distal) end of the wing may include a fastener component 118 or be affixed to another part of the chassis 112. The widths and lengths of the stretch zones and non-stretch zones may vary.

In FIG. 3B, a second embodiment of the wing 120 is shown. In this embodiment, the wing may have multiple stretch zones 126 and multiple non-stretch zones 122, 124. In this embodiment, the stretch zones alternate with the non-stretch zones. But, in other embodiments (not shown), multiple stretch zones and multiple non-stretch zones maybe grouped together. The one (or proximal) end, e.g., a non-stretch zone, of the wing 120 is affixed to the attachment surface 114 of the chassis 112 via bond 116. The other (or distal) end of the wing may include a fastener component 118 or be affixed to another part of the chassis 112. The widths and lengths of the stretch zones and non-stretch zones may vary.

In FIG. 3C, a third embodiment of wing 120 is shown. In this embodiment, the wing has a different order of stretch zones 126 and non-stretch zones 124. The one (or proximal) end, e.g., a stretch zone, of the wing 120 is affixed to the attachment surface 114 of the chassis 112 via bond 116. The other (or distal) end of the wing may include a fastener component 118 or be affixed to another part of the chassis 112. The widths and lengths of the stretch zones and non-stretch zones may vary.

One layer of non-woven extending continuously and approximately in a unique plane from an area of the layer of non-woven layer intended to be join to one attachment surface 114 of the chassis 112 to an opposite area of the layer of non-woven layer intended to be join to an opposite attachment surface 114 of the chassis 112. This unique plane may be approximately flattened when the wing is laid on a flattened support. This unique plane could be curved if the wing is joined to the chassis.

One layer of nonwoven of the wing may have a continuous path from an area near to one attachment surfaces 114 of the chassis 112 to an opposite area. The opposite area may either near to another attachment surface 114 of the chassis 112 or near to the free end of the wing, in particular near to the fastener component 118. In other word, the continuous path is defined as without passing through an interface as another layer of nonwoven or a join of two wings of multi-component wings as defined in the background.

Each of the two nonwoven layers of the wing according to the invention may have a continuous path between an area near to one attachment surface 114 of the chassis 112 and an opposite area near to an opposite attachment surface 114 of the chassis 112.

The wing 120 may have a dimension d1, see FIG. 2A (i.e., in the cross-machine direction or CD). The dimension d1 may be greater than 100 mm, 110 mm, 120 mm, 130 mm, 140 mm, 150 mm, 160 mm or 170 mm. In wing 120, d1 may be less than 400 mm. The dimension d1 may be less than 600 mm. The dimension d1 is measured, in FIG. 2A—from the chassis to the free end of the wing or in FIG. 2B—between the two opposite edges of the chassis, in particular in a direction sensibly perpendicular to a direction defined by the chassis or in a direction sensibly perpendicular to the edge of the wing bond to the chassis. The ears for the baby device have a length in CD from the chassis to the end hook tab of less than 100 mm. Wing 120 may have a dimension d2, see FIG. 2A (i.e., in the machine direction or MD) between 100 mm and 300 mm, in some embodiment between 125 mm and 250 mm. Wing 120, when used in the adult device, may have a circumference of between 400 mm and 3000 mm, or between 550 mm and 2500 mm. In some embodiment, the circumference may be 559 mm (22 inch) for a small size and may be, at least, 2438 mm (96 inches) for bariatric size (alternatively, 2591 mm (102 inches) for bariatric size, or 2693 mm (106 inches) for bariatric size). The wing may have one surface area higher than 10 000 $mm^2$, 11 000 $mm^2$, 12 000 $mm^2$, 13 000 $mm^2$, 14 000 $mm^2$, 15 000 $mm^2$, 16 000 $mm^2$, 17 000 $mm^2$, 20 000 $mm^2$, 25 000 $mm^2$, 30 000 $mm^2$, 35 000 $mm^2$, 40 000 $mm^2$. The wing may have one surface area between 11 000 $mm^2$ and 200 000 $mm^2$, in particular between 11 000 $mm^2$ and 150 000 $mm^2$, in particular between 15 000 $mm^2$ and 120 000 $mm^2$, in particular between 50 000 $mm^2$ and 85 000 $mm^2$. The wing may have one surface area between 50,000 mm2 and 150,000 mm2. The dimension of the wing is measured when the wing is at a relaxed stage, just before using it, for example just after removing it from the bag.

Figure 1A:
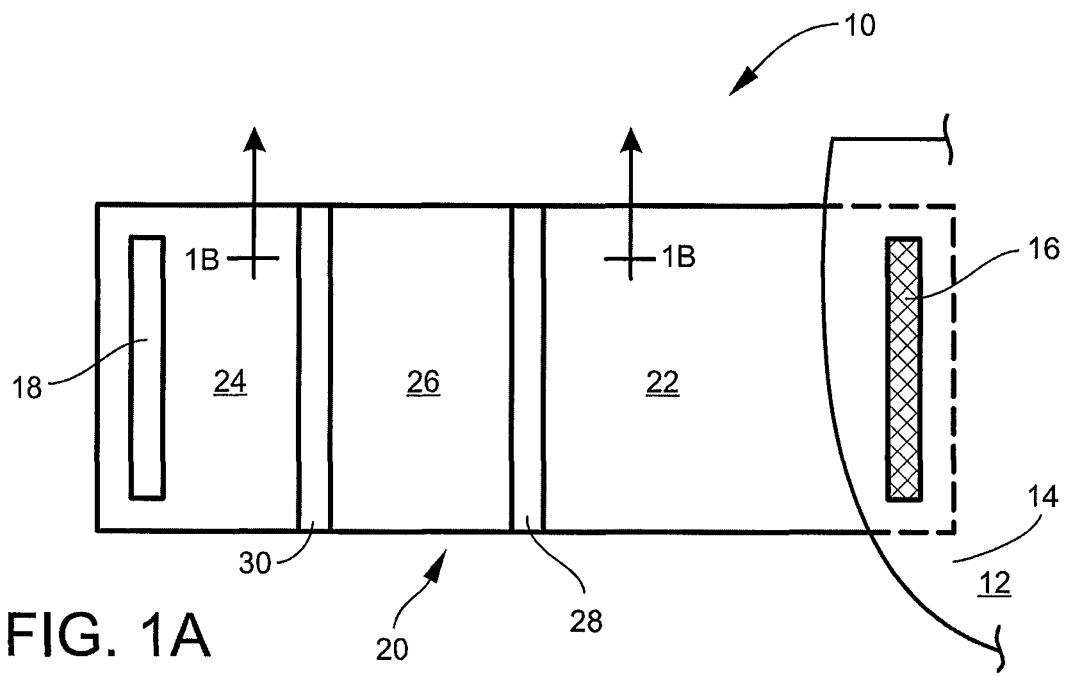
FIGS. 1A and 1B illustrate a conventional (prior art) wing used in adult incontinent devices, the FIG. 1B is a cross sectional view of the wing of the FIG. 1A according to the cut 1B-1B.

The 'capacity of utilization' of the one elastic layer of the wing may be defined by the following ratio: B"/B', see FIG. 1B. In general, 'capacity of utilization' indicates the portion of the elastic layer that is used for stretching and represents waste (or underutilization of the elastic layer—the elastic layer is relatively more expensive that the nonwoven layer and un-utilized elastic increases the cost of the device without increased benefit). For the prior art wing, generally represented in FIGS. 1A and 1B, the 'capacity of utilization' of the one elastic layer of the wing is around 60% (or 40% of the elastic layer of the wing is not utilized (or un-utilized) for elasticity). The 'capacity of utilization' of the one elastic layer of the wing according to the invention is approximately 100%. The wing 120 has a reduced cost when compared to prior art wings.

The present invention may be directed to the adult devices and may have no applicability to baby devices (or not directed to the baby devices). However, some aspects of the invention may have applicability to baby devices.

Figure 1B:
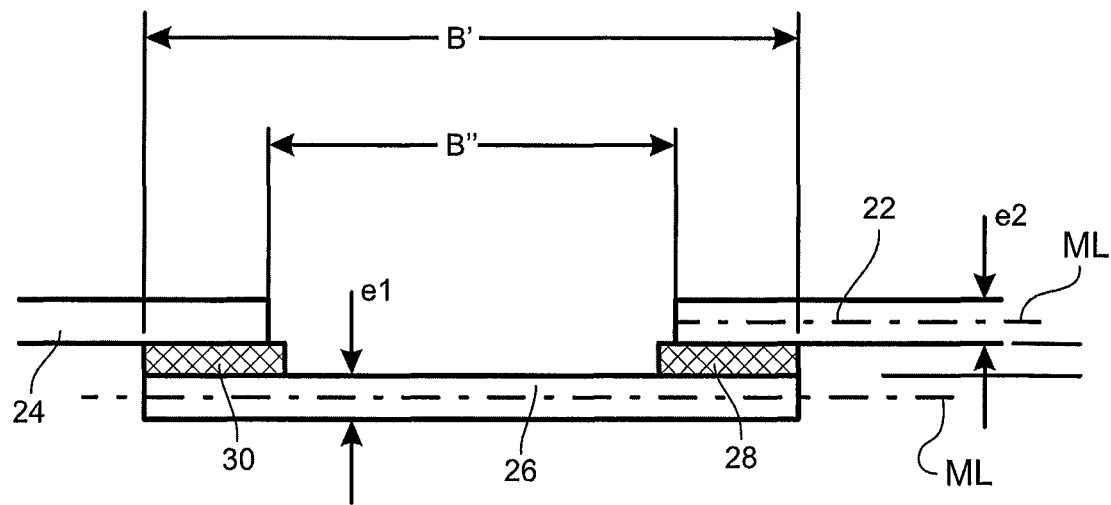

Referring to FIG. 1B, one stretch zone may have a middle line ML extending in the middle of the stretch zone in parallel of the two opposite outside faces of the stretch zone, in MD direction and/or in CD direction. In other words, the middle line ML of the stretch zone extending in the thickness of the stretch zone. One non-stretch zone may have one middle line ML extending in the middle of the non-stretch zone in parallel of the two opposite outside faces of the non-stretch zone, in MD direction or in CD direction. In other words, the middle line ML of the non-stretch zone extending in the thickness of the non-stretch zone. In the invention, a middle line ML of one stretch zone and a middle line of one adjacent non-stretch zone may be the same. In the invention, one middle line of the stretch zone and a middle line of one adjacent non-stretch zone may define a gap G. The gap is less than 50% of the thickness of the stretch zone and/or the gap G is less than 50% of the thickness of the non-stretch zone. In some embodiments, the gap may be less than one of the following rate 45%, 40%, 35%, 30%, 25%, 20% or 15% of the thickness of one stretch zone and/or one non-stretch zone. The gap may be between 0 mm and 15 mm, in particular between 0 mm and 10 mm, in particular between 0 mm and 5 mm, in particular between 0 mm and 2 mm, in particular between 0 mm and 1 mm. The thicknesses of the stretch zone and the non-stretch zone may be measured with the method described in ASTM D3774-96 (2004).

A stretch zone is a zone having an elastic set less than a non-stretch zone. A stretch zone may be a zone having elastic set less than 40%, in particular less than 20%. The elastic set may be measured according to the method described in ASTM D2731-15.

The stretch zone and/or the non-stretch zone may be aperture in full width or partially. Regarding aperture, in general, reference is made to U.S. patent application Ser. No. 15/489,812, which is incorporated herein by reference.

One elastic layer may have a middle line extending in the middle of the elastic layer in parallel of the two opposite outside faces of the elastic layer, in MD direction and/or in CD direction. One nonwoven layer may have a middle line extending in the middle of the nonwoven layer in parallel of the two opposite outside faces of the nonwoven layer, in MD direction or in CD direction. In other words, the middle line of a nonwoven layer extends in the thickness of the nonwoven layer. In the invention, a middle line of one elastic layer and a middle line of one adjacent nonwoven layer may be the same. In the invention, one middle line of the elastic layer and one middle line of one adjacent nonwoven layer may define a gap. The gap is less than 50% of the thickness of the elastic layer and/or the gap is less than 50% of the thickness of the nonwoven layer. In some embodiments, the gap may be less than one of the following rate 45%, 40%, 35%, 30%, 25%, 20% or 15% of the thickness of one elastic layer and/or one nonwoven layer. The gap may be between 0 mm and 15 mm, in particular between 0 mm and 10 mm, in particular between 0 mm and 5 mm, in particular between 0 mm and 2 mm, in particular between 0 mm and 1 mm. The gap ("gap") according to the FIG. 1B (Prior art) is at least 400% of the thickness (e1, e2) respectively of the stretch zone and the non-stretch zone. The thicknesses of the elastic layer and the nonwoven layer may be measured according to the method described in ASTM D3774-96(2004).

An elastic layer is a layer having an elastic set less than a nonwoven layer. An elastic layer may be a zone having elastic set less than 40%, in particular less than 20%. The elastic set may be measured according to the method described in ASTM D2731-15.

The elastic layer and/or the nonwoven layer may be apertured in full width or partially. Apertured, as used herein, means that the wing (or stretch laminate) is provided with a plurality of holes or small holes, so that that the wing (or stretch laminate) may breathe when in contact with the wearer (or in contact with the wearer's skin). The apertures may be any aperture that is sufficient to provide breathability (or comfort) to the wearer. In one embodiment, the aperture may have an area of 0.2-0.6 mm$^2$. In another the area may be of 0.30-0.50 mm$^2$. In another, the area may be of 0.02-0.20 mm$^2$. In yet another embodiment, the area may be about 0.04 mm$^2$. The apertures may be formed by pins (or heated pins). In one embodiment, the number of apertures may be in the range of 2-6 apertures/cm$^2$. In another embodiment, the number of apertures may be in a range of 3-5 apertures/cm$^2$. In yet another embodiment, the apertures may be in about 4/cm$^2$. The wing (or stretch laminate) may be fully or partially apertured. The wing (or stretch laminate) may have at least 45% or 50% or 60% or 70%, or 80%, or 90%, or 95% of the surface area of the wing (or stretch laminate) apertured.

The stretch laminate may comprise at least one pattern of adhesive layer. One stretch zone may have a pattern of adhesive layer and one non-stretch zone may have a pattern of adhesive layer, the pattern of adhesive layer of the stretch zone and the pattern of adhesive layer of the non-stretch zone may be similar, in particular are in full shape or in stripe shape extending in machine direction and spaced in cross direction. The stretch laminate may comprise a unique pattern of adhesive layer. One stretch zone may have a pattern of adhesive layer and one non-stretch zone may have a pattern of adhesive layer, the pattern of adhesive layer of the stretch zone may be different of the pattern of adhesive layer of the non-stretch zone, in particular in full shape in the non-stretch zone and in stripe shape extending in machine direction and spaced in cross direction in the stretch zone.

Figure 5A:
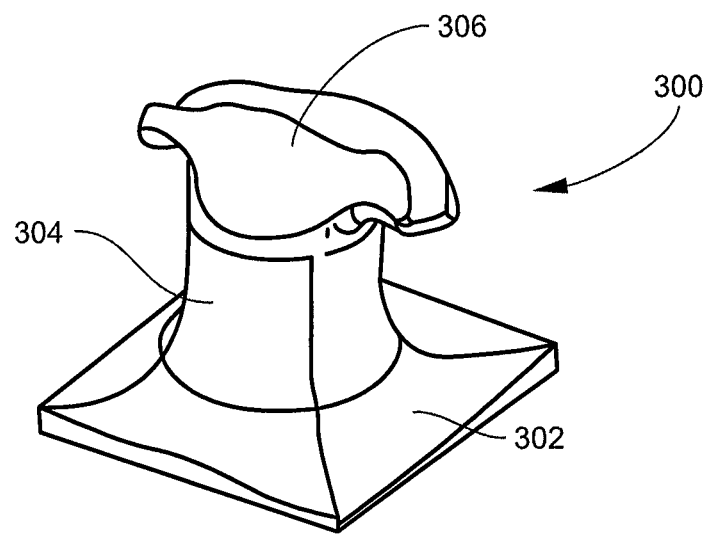
FIGS. 5A and 5B illustrate an embodiment of a hook and a ribbon carrying a plurality of hooks.
Figure 5B:
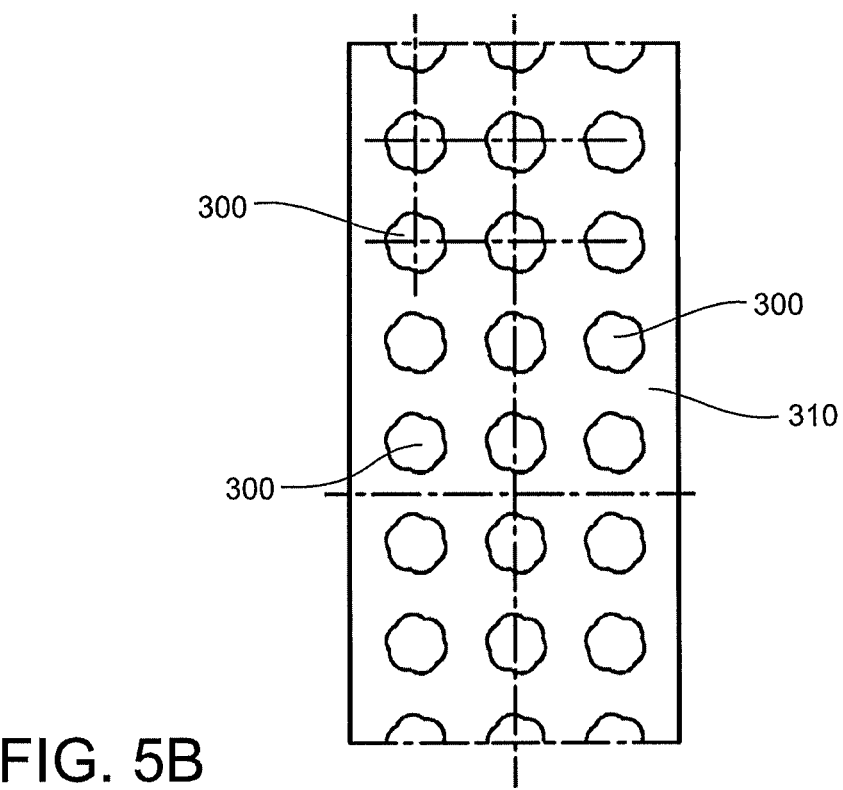

The fastener components 118 and 118A, note the embodiment illustrated in FIG. 2A, may be a hook and loop fastener. The hook and loop fastener may be any hook and loop fastener. In FIGS. 5A and 5B, one embodiment of a hook 300 is illustrated and is further disclosed in WO2017187096; WO2017187097; and WO2017187098, each incorporated herein by reference. FIG. 5A shows that hook 300 has a base 302, a stem 304, and a cap 306. Cap 306 has a greater diameter than stem 304. In FIG. 5B, a plurality of hooks 300 may be disposed (or formed with or formed integrally with) a ribbon 310.

Fastener component 118 (which may be hooks or mushroom) may be affixed along a lateral edge portion or the roll good. In FIGS. 6B and 6C, fastener components 118 (which may be hooks or mushroom) may be affixed along a center portion of the roll, or along the lateral edge portions of the roll good.

Figure 7:
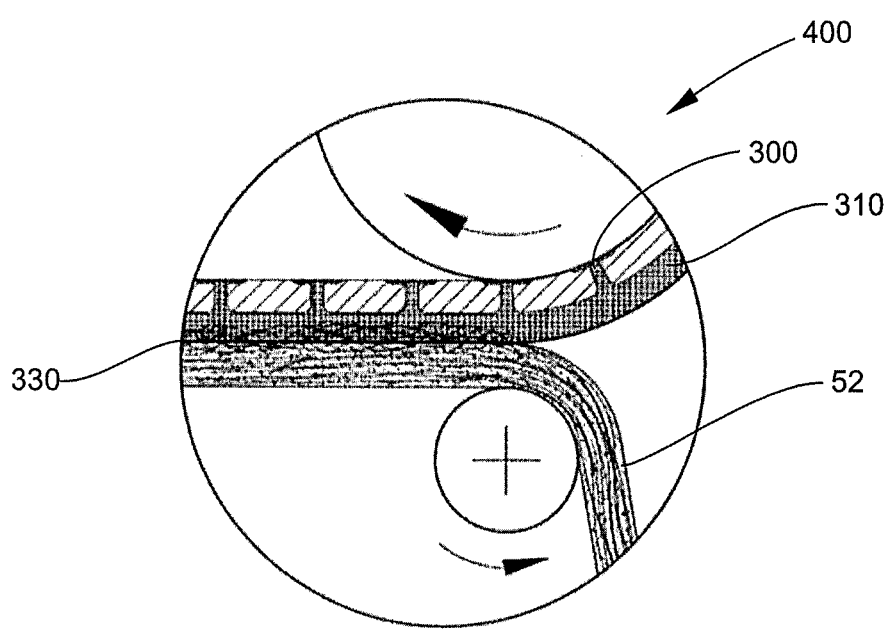
FIG. 7 illustrates an embodiment of a method for joining a fastener component with the invention.

The fastener may be manufacture by using a molding apparatus, comprising a molding belt. The molding belt may be mounted on rotating drive means (for example, comprising at least two rollers), the molding belt comprising an inner face and an outer face, the inner face being mounted against the rotating drive means, the molding belt comprising a plurality of cavities, each cavity defining a stem extending from the outer face towards the inner face, and comprising an end forming a head extending from the stem towards the inner face of the molding belt. In a next steep, a molding material may be distributed on the outer side of the molding belt by a material distribution means arranged opposite the molding belt so as to define an air gap between the material distribution means and the molding belt, the step of dispensing the molding material being carried out so as to fill said air gap and the molding material cavities to form a tape comprising a base the thickness of which is defined by the air gap, and the stem and the head, the stem and the head being formed by the plastic material in the cavities of the molding belt, the stem and the head being demolded in order to obtain directly or indirectly the fastener. The process of manufacture is illustrated and is further disclosed in WO2017187096; WO2017187097; WO2017187098, WO2017187099; WO2017187101; WO2017187102 and WO2017187103 each incorporated herein by reference. FIG. 7 illustrates an embodiment of the method 400 for affixing a thermoplastic ribbon 310 of hooks 300 to a nonwoven (e.g., 52 and/or 54) via an autogenous bond 330. While bond 330 is illustrated as pressing the softened thermoplastic of the ribbon into the nonwoven (e.g., without the use of adhesive), the bond may be formed with an adhesive and/or by welding (e.g., thermal and/or ultrasonic).

Figure 6A:
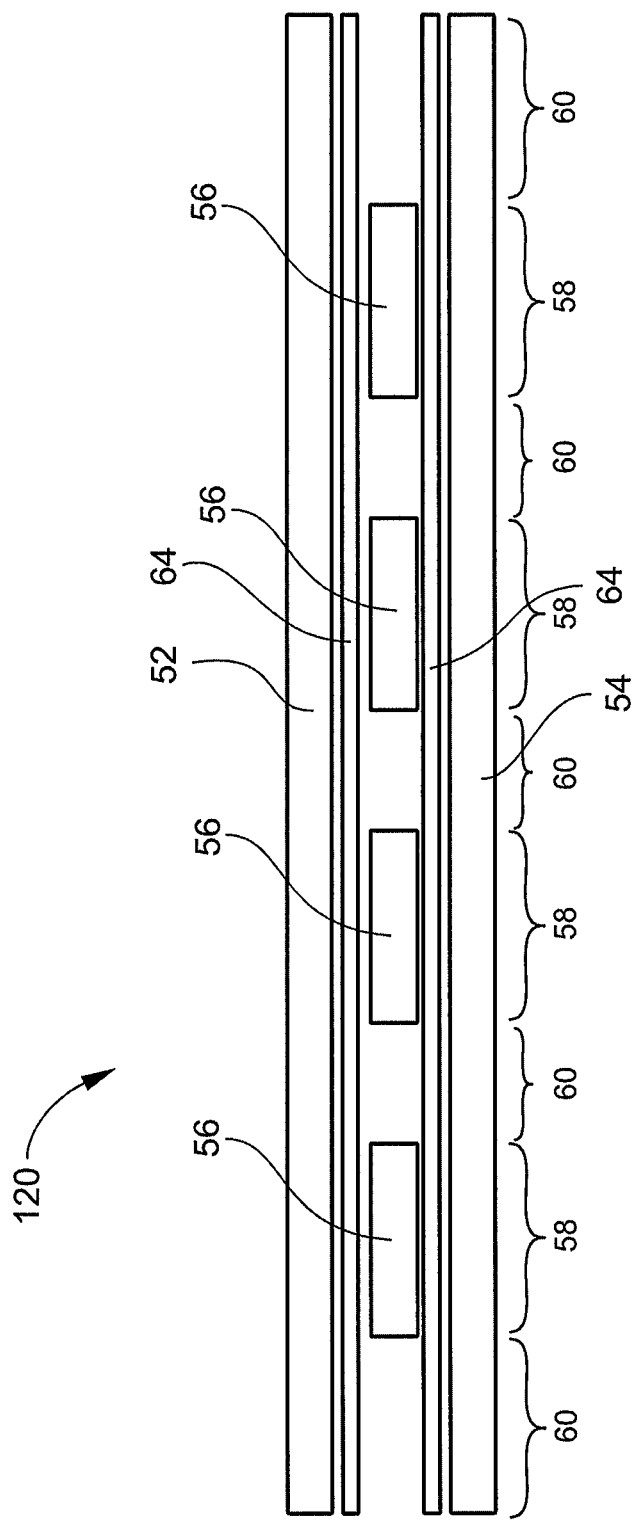

In use, wings 120 may be supplied in roll form (or roll goods). The wings 120 may be disposed across the width of the roll and down the length of the roll. Any number of wings 120 may be disposed across the width of the roll and down the length of the roll. FIG. 6A illustrates a cross-section of an embodiment of a roll with four stretch zones 58 and five non-stretch zones 60. FIG. 6B illustrates a cross-section of an embodiment of a roll with a single wing 120 with two stretch zones 58 and three non-stretch zones 60. FIG. 6C illustrates a cross-section of an embodiment of a roll with two wings 120 (note the dashed dividing line) disposed across the width of the roll. For the wing illustrated on FIG. 6B, the dimension d1 is 288 mm, d2 is 240 mm, the width of the elastic lanes are equal and that width is 45 mm, the wing have a surface area of 69,120 mm$^2$, the middle line of the stretch zone and the middle line of the non-stretch zone are the same, thus the gap is 0 mm. For wing illustrated on FIG. 6C, the dimension d1 is 288 mm, d2 is 240 mm, the width of the elastic lanes are equal and that width is 45 mm, the wing have a surface area of 69,120 mm$^2$, the middle line of the stretch zone and the middle line of the non-stretch zone are the same, thus the gap is 0 mm.

The present invention may be embodied in other forms without departing from the spirit and the essential attributes thereof, and, accordingly, reference should be made to the appended claims, rather than to the foregoing specification, as indicated the scope of the invention.

We claim:

1. A method for making an adult incontinent device comprising the steps of:

providing a chassis for the adult incontinent device, the chassis having a lateral attachment surface;

affixing a wing to the lateral attachment surface, the wing is a stretch laminate with at least one nonwoven layer and at least one elastic layer, the nonwoven layer and the elastic layer are bound together in face-to-face contact, the stretch laminate has at least one stretch zone and at least one non-stretch zone, the stretch laminate has no overlap portions between the stretch zone and the non-stretch zone; and thereby forming the adult incontinent device; wherein the non-stretch zone comprises no elastic layer.

2. The method of claim 1 wherein the wing has one stretch zone located between two non-stretch zones, and one non-stretch zone is affixed to the lateral attachment surface.

3. The method of claim 1 wherein the wing has at least two stretch zones and at least three non-stretch zones, the stretch zones and the non-stretch zones alternating across the wing, and one non-stretch zone is affixed to the lateral attachment surface.

4. The method of claim 1 wherein the wing has at least two stretch zones and at least one non-stretch zone, the stretch zones and the non-stretch zones alternating across the wing, and one stretch zone is affixed to the lateral attachment surface.

5. The method of claim 1 wherein the stretch laminate comprises a first nonwoven, a second nonwoven, and elastic film sandwiched therebetween.

6. The method of claim 1 wherein the nonwoven is a spunbond nonwoven.

7. The method of claim 1 wherein the stretch zone comprises a laminate of the nonwoven layer and the elastic layer.

8. The method of claim 1 wherein the elastic layer is: activated, non-activated, partially activated; and/or activated to varying degrees.

9. The method of claim 1 wherein the wing further comprises hooks affixed at an end of the wing opposite the lateral attachment surface.

10. The method of claim 1 wherein the wing has a dimension (d1) and d1 is greater than 100 mm.

11. The method of claim 1 wherein the stretch laminate having no overlap portions between the stretch zone and the non-stretch zone is characterized by the nonwoven layer having a continuous path from the lateral attachment area to either another lateral attachment area on the chassis or a free end of the wing.

12. The wing of claim 11 wherein the stretch zone comprises a laminate of the nonwoven layer and the elastic layer.

13. A wing for an adult incontinent device, the device has a chassis for the adult incontinent device, the chassis has a lateral attachment surface, comprises:

a stretch laminate with at least one nonwoven layer and at least one elastic layer, the nonwoven layer and the elastic layer are bound together in face-to-face contact, the stretch laminate has at least one stretch zone and at least one non-stretch zone, the stretch laminate has no overlap portions between the stretch zone and the non-stretch zone, and one end of the wing is affixed to the lateral attachment surface of the chassis;

wherein the non-stretch zone comprises no elastic layer.

14. The wing of claim 13 further comprising one stretch zone located between two non-stretch zones, and one non-stretch zone is affixed to the lateral attachment surface.

15. The wing of claim 13 further comprising at least two stretch zones and at least three non-stretch zones, the stretch zones and the non-stretch zones alternating across the wing, and one non-stretch zone is affixed to the lateral attachment surface.

16. The wing of claim 13 further comprising at least two stretch zones and at least one non-stretch zone, the stretch zones and the non-stretch zones alternating across the wing, and one stretch zone is affixed to the lateral attachment surface.

17. The wing of claim 13 wherein the stretch laminate comprises a first nonwoven, a second nonwoven, and elastic film sandwiched therebetween.

18. The wing of claim 13 wherein the nonwoven is a spunbond nonwoven.

19. The wing of claim 13 wherein the elastic layer is: activated, non-activated, partially activated; and/or activated to varying degrees.

20. The wing of claim 13 further comprises hooks affixed at an end of the wing opposite the lateral attachment surface.

21. The wing of claim 13 further comprises a dimension (d1) and d1 is greater than 100 mm.

22. The wing of claim 13 wherein the stretch laminate having no overlap portions between the stretch zone and the non-stretch zone is characterized by the nonwoven layer having a continuous path from the lateral attachment area to either another lateral attachment area on the chassis or a free end of the wing.

23. An adult incontinent device comprises:

a chassis with a lateral attachment surface, and a wing including a stretch laminate with at least one nonwoven layer and at least one elastic layer, the nonwoven layer and the elastic layer are bound together in face-to-face contact, the stretch laminate has at least one stretch zone and at least one non-stretch zone, the stretch laminate has no overlap portions between the stretch zone and the non-stretch zone, and one end of the wing is affixed to the lateral attachment surface of the chassis: wherein the non-stretch zone comprises no elastic layer.

24. The adult incontinent device of claim 23 further comprising one stretch zone located between two non-stretch zones, and one non-stretch zone is affixed to the lateral attachment surface.

25. The adult incontinent device of claim 23 further comprising at least two stretch zones and at least three non-stretch zones, the stretch zones and the non-stretch zones alternating across the wing, and one non-stretch zone is affixed to the lateral attachment surface.

26. The adult incontinent device of claim 23 further comprising at least two stretch zones and at least one non-stretch zone, the stretch zones and the non-stretch zones alternating across the wing, and one stretch zone is affixed to the lateral attachment surface.

27. The adult incontinent device of claim 23 wherein the stretch laminate comprises a first nonwoven, a second nonwoven, and elastic film sandwiched therebetween.

28. The adult incontinent device of claim 23 wherein the nonwoven is a spunbond nonwoven.

29. The adult incontinent device of claim 23 wherein the stretch zone comprises a laminate of the nonwoven layer and the elastic layer.

30. The adult incontinent device of claim 23 wherein the elastic layer is: activated, non-activated, partially activated; and/or activated to varying degrees.

31. The adult incontinent device of claim 23 further comprises hooks affixed at an end of the wing opposite the lateral attachment surface.

32. The adult incontinent device of claim 23 further comprises a dimension (d1) and d1 is greater than 100 mm.

33. The adult incontinent device of claim 23 wherein the stretch laminate having no overlap portions between the stretch zone and the non-stretch zone is characterized by the nonwoven layer having a continuous path from the lateral attachment area to either another lateral attachment area on the chassis or a free end of the wing.

* * * * *